United States Patent [19]

Sweeney et al.

[11] Patent Number: 5,221,544

[45] Date of Patent: * Jun. 22, 1993

[54] PRODUCTION OF DIETARY FATTY ACID SALT PRODUCTS

[75] Inventors: Thomas F. Sweeney, Morrisville, Pa.; M. Stephen Lajoie, Basking Ridge, N.J.; Alfredo Vinci, Dayton, N.J.; Kenneth R. Cummings, Basking Ridge, N.J.

[73] Assignee: Church & Dwight Co., Inc., Princeton, N.J.

[*] Notice: The portion of the term of this patent subsequent to Mar. 2, 2010 has been disclaimed.

[21] Appl. No.: 802,266

[22] Filed: Dec. 4, 1991

[51] Int. Cl.$^5$ .............................. A23K 1/00
[52] U.S. Cl. ........................ 426/72; 426/74; 426/601; 426/648; 426/656; 426/658; 426/807; 514/558
[58] Field of Search .............. 426/72, 74, 601, 656, 426/658, 648, 807; 514/558

[56] References Cited

U.S. PATENT DOCUMENTS

| | | | |
|---|---|---|---|
| 4,729,896 | 3/1988 | Sawhill | 426/647 |
| 4,826,694 | 5/1989 | McAskie | 426/74 |
| 4,994,284 | 2/1991 | Miller | 426/69 |
| 5,063,067 | 11/1991 | Binder et al. | 426/807 |
| 5,132,123 | 7/1992 | Laiho et al. | 426/74 |

OTHER PUBLICATIONS

Lakota et al. "Fatty acid salts for feeds" Chemical Abstracts vol. 95 p. 607, 1981 Abstract No. 95:78791q.
Hawley "The Condensed Chemical Dictionary" 10th edition Van Nostrand Reinhold Co (1982) p. 947.

*Primary Examiner*—R. B. Penland
*Attorney, Agent, or Firm*—Charles B. Barris

[57] ABSTRACT

In one embodiment this invention provides an improved process for the production of fatty acid calcium salt. An important feature of the process is the utilization of a residual effluent byproduct stream from a sodium bicarbonate manufacturing plant as the aqueous medium of the fatty acid calcium salt-forming reaction process.

A product of the invention process is a fatty acid salt dietary supplement composition which contains one or more additional biologically active nutrient or medicament ingredients.

21 Claims, No Drawings

PRODUCTION OF DIETARY FATTY ACID SALT PRODUCTS

CROSS-REFERENCE TO RELATED APPLICATION

The subject matter of the present patent application is related to that disclosed in patent application Ser. No. 761,234, filed Sept. 17, 1991.

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is a concentrated energy source, and it is known that if the proportion of fat in cattle feed is increased, lactating dairy cattle produce high milk yields without draining their reserves of body fat and without diminishing the proportion of milk fat in the milk produced.

However, it has been found that if the proportion of fat in the diet of cattle exceeds about 5% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, the total energy derived is less than that resulting from more complete microbial digestion in the rumen.

There has been a continuing need for new dietary supplements for animal feed which can be fed to ruminant animals without interfering with the rumen microorganisms or being rendered ineffective by the rumen microorganisms.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen inert product which passes through the rumen without interfering with rumen fermentation (i.e, a rumen bypass product), and is subsequently metabolized in the abomasum or small intestine of the ruminant.

Also of background interest with respect to the present invention are the important environmental ramifications of the generation and accumulation and disposal of residual effluent streams from chemical manufacturing industries. Stringent waste disposal regulations have spurred the search for ecologically acceptable means of chemical byproduct disposal or utilization.

Accordingly, it is an object of the invention to provide a fatty acid salt composition which can function as a rumen bypass animal feed supplement, and permit a beneficial increase in the dietary fat content of the feed.

It is another object of this invention to provide a novel process for production of a fatty acid salt, in which a residual byproduct effluent from a chemical manufacturing operation is incorporated as a reactive aqueous medium.

It is a further object of this invention to provide a process for production of a fatty acid salt dietary supplement composition which contains one or more additional biologically active nutrient or medicament ingredients which have rumen bypass protection.

Other objects and advantages of the present invention shall become apparent from the accompanying description and examples.

DESCRIPTION OF THE INVENTION

One or more objects of the present invention are accomplished by the provision of a process for the preparation of a dietary fatty acid salt product which comprises (I) forming an admixture of reactive ingredients comprising (A) at least one $C_{14}$–$C_{22}$ fatty acid, (B) calcium oxide in about a 0.8–1.2 equivalent weight quantity per equivalent of $C_{14}$–$C_{22}$ fatty acid, (C) between about 10–50 weight percent, based on the weight of fatty acid, of an aqueous solution of sodium carbonate-bicarbonate, wherein the aqueous solution is a residual effluent from a sodium bicarbonate-producing process, and the solution contains between about 0.2–5 weight percent of sodium in the form of sodium carbonate-bicarbonate, and (D) an aqueous suspension medium containing constituents comprising (a) $C_{14}$–$C_{22}$ fatty acid alkali metal or ammonium salt, and (b) a biologically active ingredient; and (2) recovering the salt product after completion of the salt-forming reaction.

The (A) $C_{14}$–$C_{22}$ fatty acid component of the salt-forming reaction medium consists of one or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| Free fatty acids | 60–90 |
|---|---|
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| Palmitic acid | 38–50 |
|---|---|
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| Free fatty acids | 60–90 |
|---|---|
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| | |
|---|---|
| Palmitic acid | 22–28 |
| Oleic acid | 38–44 |
| Linoleic acid | 3–6 |
| Stearic acid | 18–24 |

Because $C_{14}$–$C_{22}$ fatty acids and glycerides are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid.

Illustrative of preferred additives are butylated hydroxytoluene antioxidant, and citric acid and ethylenediamine tetraacetate chelating agents. The chelating agent is added in an edible solvent such as propylene glycol to facilitate blending into the fatty acid.

The calcium oxide component of the process can be utilized either alone or in combination with magnesium oxide. The calcium oxide component can be calcined limestone, which contains 93–96% CaO and not more than about 7% of $CaCO_3$. The basic oxide preferably has a particle size which passes a 100 mesh U.S. standard screen.

As noted previously, the (C) aqueous phase of the salt-forming reaction system is provided in the form of an aqueous solution of sodium carbonate-bicarbonate. The aqueous solution is a residual effluent from a sodium bicarbonate-producing process, and contains between about 0.2–5 weight percent of sodium in the form of a sodium carbonate-bicarbonate mixture.

The residual effluent typically is derived from a plant scale manufacturing operation in which sodium carbonate is carbonated to sodium bicarbonate. The residual effluent stream generated from the carbonation process typically has a sodium ion content of about 0.2–2 weight percent. A higher sodium content can be obtained if desired by evaporating a portion of the aqueous medium, or by utilizing a more concentrated solution such as a purge stream from the main reactor.

The (D) aqueous suspension medium of the invention process has a content of $C_{14}$–$C_{22}$ fatty acid alkali metal or ammonium salt, and a biologically active ingredient. The quantity of (D) aqueous suspension medium utilized in the process provides between about 0.01–20 weight percent of biologically active ingredient, based on the weight of (A) $C_{14}$–$C_{22}$ fatty acid.

The (D) aqueous suspension medium optionally can contain one or more additional components, and the content of water-insoluble ingredients which are suspended in the (D) aqueous suspension medium usually will be in the range of about 10–40 weight percent of medium weight. The particle size of the suspended phase generally will range from colloidal to a particle size of solid which passes through a 100 mesh U.S. standard screen.

The content of ingredients in the (D) aqueous suspension medium typically will conform to the following proportions:

| Ingredient | Weight Percent |
|---|---|
| Fatty acid salt | 15–60 |
| biologically active constituent | 5–30 |
| Carbohydrate | 0–50 |
| Suspension stabilizing agent | 0–2 |
| Antioxidant | 0–0.5 |
| Preservative | 0–1 |
| Other optional constituents | 0–30 |

The fat ingredient of the (D) aqueous suspension medium is selected from $C_{14}$–$C_{22}$ fatty acid salts of alkali metal and ammonium ions. The alkali metal ions are illustrated by sodium, potassium and lithium, and the ammonium ions are illustrated by the $H\oplus NR^3$ structure, where R is hydrogen or a $C_1$–$C_4$ alkyl substituent.

Suitable $C_{14}$–$C_{22}$ fatty acids are similar to those described above, which include myristic, palmitic, stearic, arachidic, behenic, oleic, ricinoleic, linoleic, linolenic, gadoleic, and the like, singly or in any combination. The unsaturated fatty acids typically are mixtures of cis and trans isomers.

The biologically active constituent of an invention (D) aqueous suspension medium can be selected from a broad variety of nutrients and medicaments, either as a single component or as a mixture of components, which are illustrated by the following listing of active molecular species:

1. $C_2$–$C_{22}$ aliphatic carboxylic acids and esters, and alkali metal, ammonium and alkaline earth metal salts which are different than the selected (A) fatty acid salt ingredient of the process.

2. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

| | |
|---|---|
| Protein | 12.0% |
| Fat | 0.7% |
| Lactose | 60.0% |
| Phosphorus | 0.79% |
| Calcium | 0.87% |
| Ash | 9.7% |

Another source of carbohydrate is derived from the pulp and paper industry which produces large quantities of byproduct lignin sulfonates from wood during the sulfite pulping process. The byproduct is recovered in the form of salts such as ammonium, sodium and magnesium lignin sulfonates.

3. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs thereof.

4. vitamin ingredients either singly or in combination which include thiamine HCl, riboflavin, pyridoxine HCl, niacin, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

5. protein ingredients as obtained from sources such as dried blood or meat meal, cottonseed meal, soy meal, dehydrated alfalfa, dried and sterilized animal and poultry manure, fish meal, liquid or powdered egg, fish solubles, cell cream, and the like.

Protein equivalent ingredients include non-protein nitrogen compounds such as urea, biuret, ammonium phosphate, and the like.

6. medicament ingredients either singly or in combination which include promazine hydrochloride, chloromadionate acetate, chlorotetracycline, sulfamethazine, monensin, sodium monensin, poloxaline, and the like. Oxytetracycline is a preferred antibiotic for cattle prophylaxis.

7. enzymes such as lipolytic proteins which aid feed digestibility, e.g., by hydrolysis of fatty acid glycerides to free fatty acid and glycerol.

8. antioxidants as illustrated by butylated hydroxyanisole, butylated hydroxytoluene, tertiary-butylhydroquinone, propyl gallate, and ethoxyquin; and suitable preservatives include sodium sorbate, potassium sorbate, sodium benzoate, propionic acid, α-hydroxybutyric acid, and the like.

9. suspension stabilizing agents which preferably are selected from nonionic surfactants, hydrocolloids and cellulose ethers. These types of chemical agents are illustrated by polyethylene oxide condensates of phenols, $C_8$–$C_{22}$ alcohols and amines; ethylene oxide reaction products with fatty acid partial esters of hexitans; alkylarylpolyoxyethylene glycol phosphate esters; gum arabic; carob bean gum; guar gum; tragacanth gum; ammonium, sodium, potassium and calcium alginates; glycol alginates; xanthan gum; potato agar; alkylcellulose; hydroxyalkylcellulose; carboxyalkylcellulose; and the like.

A (D) aqueous suspension medium is prepared by adding the selected ingredients successively to the aqueous medium with stirring. One or more ingredients also can be premixed before addition to the aqueous medium, such as a mixture of fatty acids, or a vitamin or trace element premix composition.

It is advantageous to utilize high shear mixing when a suspension medium with a large proportion of water-insoluble solids is being homogenized. An inorganic powder such as magnesium oxide which undergoes hydration preferably is added as the first ingredient to the aqueous medium in order to minimize agglomeration of the fine particles.

The pH of a (D) aqueous suspension medium can be adjusted by the addition of ammonium hydroxide, potassium hydroxide, orthophosphoric acid, hydrochloric acid, acetic acid, citric acid, or the like, as appropriate to achieve the desired pH level.

The invention process can be conducted in a batch reactor or as a continuous operation. The (A) $C_{14}$–$C_{22}$ fatty acid, (B) calcium oxide, (C) aqueous solution and (D) aqueous suspension medium can be admixed simultaneously, or there can be premixing of two or more ingredients. It is convenient to premix the (C) aqueous solution of sodium carbonate-bicarbonate with the (D) aqueous suspension medium, and the (A) $C_{14}$–$C_{22}$ fatty acid with the (B) calcium oxide.

In one method the fatty acid is heated to 60°–110° C. or higher, and then mixed with the basic oxide. After the (C) aqueous solution and (D) aqueous suspension medium are added to the mixture, there is a short induction period which is followed by an exothermic salt-forming reaction.

The amount of water employed in the process is sufficient to support the salt-forming reaction, and preferably is vaporized as steam during the exothermic reaction period to yield a friable fatty acid salt product which in granule form is suitable for use as an animal feed supplement.

An important advantage of the present invention process is the value-added utilization of a residual effluent from a chemical manufacturing plant, which has both environmental and economic consequences.

Another advantage of the invention process is in the efficiency of insoluble fatty acid calcium salt formation. It appears that the sodium carbonate-bicarbonate salt present in the aqueous medium component reacts readily with the fatty acid component to form an intermediate fatty acid sodium salt. Subsequently the fatty acid sodium salt interacts with the hydrated calcium oxide to produce the insoluble fatty acid calcium salt product. If the sodium content in the original aqueous effluent stream is at least about 1.0 weight percent, the kinetically favorable sodium salt intermediate reaction converts essentially all of the fatty acid from free acid to a sodium salt intermediate. Without the presence of the basic sodium ions, the kinetically less favorable reaction of calcium ions with fatty acid tends to be incomplete and some residual unreacted fatty acid remains under the processing conditions. The presence of sodium ions facilitates the conversion of fatty acid via the sodium salt intermediate to its calcium salt derivative.

A present invention fatty acid salt product is adapted to function as a rumen bypass dietary supplement in ruminant feed. An important advantage of a present invention dietary supplement composition is the rumen bypass protection which extends to all the biologically active ingredients of the composition, such as aminoacids, vitamins, and the like, which normally are metabolized in the rumen.

The following Examples are further illustrative of the present invention. The components and specific ingredients are presented as being typical, and various modifications can be derived in view of the foregoing disclosure within the scope of the invention.

EXAMPLE I

This Example illustrates the preparation of aqueous suspension medium formulations containing an aminoacid ingredient, which are suitable for incorporation as a fluid component in the invention process.

| | |
|---|---|
| Potassium oleate | 350 g |
| Potassium stearate | 350 g |
| Palmitic acid | 100 g |
| Methionine hydroxy analog | 200 g |

The ingredients are added in the listed order to one liter of water with high speed stirring.

The viscosity of the resultant emulsion is measured on a Brookfield viscometer with a number 6 spindle at 12 rpm. The emulsion has a viscosity of about 300 centipoises, and a pH of 8.

Another emulsion is prepared in the described manner except that two grams of guar gum are added to the liter of water before the other ingredients. The measured viscosity of the emulsion is about 800 centipoises.

Another emulsion is prepared except that 20 grams of sucrose are dissolved in the liter of water before the other ingredients are added. The viscosity of the emulsion is about 900 centipoises.

Another emulsion is prepared except that 20 grams of whey solids are dissolved in the liter of water, and then 2 grams of polyethylene glycol (400) monooleate are added with stirring before the other ingredient additions. The viscosity of the emulsion is about 1500 centipoises.

EXAMPLE II

This Example illustrates the continuous production of a dietary fatty acid calcium salt product in accordance with the present invention.

The fatty acid component is a palm fatty acid distillate of the following composition:

| | |
|---|---|
| Lauric acid | 2.3% |
| Palmitic acid | 49.9% |
| Stearic acid | 5.4% |
| Oleic acid | 35.0% |
| Linoleic acid | 7.4% |

The residual effluent aqueous solution is obtained from a Church & Dwight Co., Inc. sodium bicarbonate manufacturing plant in Old Fort, Ohio. The aqueous medium contains about 4.2% sodium carbonate-bicarbonate.

Each of the aqueous suspension media described in Example I is used in separate processing runs, respectively. Each aqueous suspension medium is provided in bulk quantity with the weight ratio of ingredients listed in Example I.

The process is operated continuously with equipment which is essentially the same as described and illustrated with reference to FIG. 1 of U.S. Pat. No. 4,826,694 by W. McAskie.

Calcium oxide from a hopper and hot palm oil distillate (96° C.) from a supply line are mixed in predetermined proportions in a mixing pump.

The residual effluent aqueous solution and aqueous suspension medium are fed to a mixing pump, and the resultant combined stream is added to the reaction mixture by a supply line. The quantity of water in the reaction mixture is about 30 weight percent, and the quantity of methionine hydroxy analog is about 0.05 weight percent, based on the weight of fatty acid component.

The hydrated mixture is passed through a mixing pump and the resultant semi-liquid reaction medium at about 100° C. is discharged as a spread layer onto a continuously moving conveyor belt. Steam and carbon dioxide evolve from the conveyor transported reaction mass.

At the end of the conveyor belt solid lumps of reaction product fall through a sizing machine onto a second conveyor belt. In this conveying zone the salt-forming reaction and evolution of water proceed to completion. The essentially dry fatty acid calcium salt product is passed through a sifter, and collected in bags suitable for transportation and storage.

The residence time on the first conveyor is about 30 minutes, and the overall production time from reactant mixing to collection of the dry granulated product is about 2.25 hours.

The final product has a total fatty acid calcium salt content of 85 weight percent, a water content of about 3-5 weight percent, and an ash content of about 15 weight percent.

The invention fatty acid calcium salt product can be incorporated as a dietary supplement in cattle feed such as hay silage or corn silage, in a calculated quantity which will provide each animal about 200 grams per day of fatty acid salt, and about two grams per day of methionine hydroxy analog.

What is claimed is:

1. A process for the preparation of a dietary fatty acid ruminant feed salt product which comprises (1) reacting an admixture of ingredients consisting essentially of (A) at least one $C_{14}$–$C_{22}$ fatty acid, (B) calcium oxide in about a 0.8–1.2 equivalent weight quantity per equivalent of $C_{14}$–$C_{22}$ fatty acid, (C) between about 10–50 weight percent, based on the weight of fatty acid, of an aqueous solution of sodium carbonate bicarbonate, wherein the aqueous solution is a residual effluent from a sodium bicarbonate-producing process, and the solution contains between about 0.2–5 weight percent of sodium in the form of sodium carbonate-bicarbonate and (D) an aqueous suspension medium containing constituents comprising (a) between about 15–60 weight percent of $C_{14}$–$C_{22}$ fatty acid alkali metal or ammonium salt, based on the weight of aqueous suspension medium, and (b) between about 0.01–20 weight percent of a biologically active ingredient, based on the weight of (A) $C_{14}$–$C_{22}$ fatty acid, and 5–30 weight percent, based on the weight of aqueous suspension medium; and (2) recovering the salt product after completion of a salt-forming reaction; wherein sodium ions facilitate conversion of said fatty acid by a sodium ion intermediate to its calcium salt.

2. A process in accordance with claim 1 wherein the (C) aqueous solution of sodium carbonate-bicarbonate and the (D) aqueous suspension medium are premixed before admixture with the other process ingredients.

3. A process in accordance with claim 1 wherein the (A) $C_{14}$–$C_{22}$ fatty acid and (B) calcium oxide are premixed before admixture with the other process ingredients.

4. A process in accordance with claim 1 wherein the (A) fatty acid ingredient is a mixture comprising 0–10 percent lauric acid, 0–60 percent palmitic acid, 0–10 percent stearic acid, 0–60 percent oleic acid, and 0–10 percent linoleic acid.

5. A process in accordance with claim 1 wherein the (D) aqueous suspension medium prior to admixture is a concentrated liquid nutrient formulation having a pH in the range between about 4–12, and a viscosity in the range between about 5–5000 cps at 25° C.

6. A process in accordance with claim 1 salt ingredient has alkali metal ions selected from sodium, potassium and lithium, or ammonium ions corresponding to the formula $H \oplus NR^3$, where R is hydrogen or a $C_1$–$C_4$ alkyl substituent.

7. A process in accordance with claim 1 wherein the biologically active ingredient is a nutrient.

8. A process in accordance with claim 1 wherein the biologically active ingredient is a medicament.

9. A process in accordance with claim 1 wherein the biologically active ingredient comprises at least one aminoacid.

10. A process in accordance with claim 1 wherein the biologically active ingredient comprises at least one polypeptide.

11. A process in accordance with claim 1 wherein the biologically active ingredient comprises at least one antibiotic.

12. A process in accordance with claim 1 wherein the biologically active ingredient comprises at least one vitamin or nutrient trace element.

13. A process in accordance with claim 1 wherein the (D) aqueous suspension medium contains a suspension stabilizing agent.

14. A process in accordance with claim 13 wherein the suspension stabilizing agent is a nonionic surfactant.

15. A process in accordance with claim 13 wherein the suspension stabilizing agent is a hydrocolloid.

16. A process in accordance with claim 13 wherein the suspension stabilizing agent is a cellulose ether.

17. A process in accordance with claim 1 wherein the (D) aqueous suspension medium contains a polysaccharide.

18. A process in accordance with claim 1 wherein the (D) aqueous suspension medium contains a water-soluble carbohydrate.

19. A process in accordance with claim 18 wherein the carbohydrate is a molasses or whey mixture.

20. A process in accordance with claim 1 wherein the salt-forming reaction medium is at a temperature between about 60°–110° C.

21. A process in accordance with claim 1 water evaporation occurs during the salt-forming reaction, and the salt product is recovered in the form of friable granules.

* * * * *